United States Patent
Andersen et al.

(10) Patent No.: US 10,619,190 B2
(45) Date of Patent: *Apr. 14, 2020

(54) COMPOSITIONS, METHODS, SYSTEMS AND KITS FOR TARGET NUCLEIC ACID ENRICHMENT

(71) Applicant: LIFE TECHNOLOGIES CORPORATION, Carlsbad, CA (US)

(72) Inventors: Mark Andersen, Carlsbad, CA (US); Steven Roman, Carlsbad, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,128

(22) Filed: Apr. 19, 2018

(65) Prior Publication Data

US 2018/0237826 A1 Aug. 23, 2018

Related U.S. Application Data

(60) Continuation of application No. 14/829,297, filed on Aug. 18, 2015, now Pat. No. 9,957,552, which is a division of application No. 14/054,618, filed on Oct. 15, 2013, now Pat. No. 9,133,510.

(60) Provisional application No. 61/714,206, filed on Oct. 15, 2012, provisional application No. 61/764,122, filed on Feb. 13, 2013.

(51) Int. Cl.
  *C12Q 1/6806* (2018.01)
  *C07H 21/00* (2006.01)
  *C12Q 1/6853* (2018.01)

(52) U.S. Cl.
  CPC ........... *C12Q 1/6806* (2013.01); *C07H 21/00* (2013.01); *C12Q 1/6853* (2013.01)

(58) Field of Classification Search
  None
  See application file for complete search history.

(56) References Cited

U.S. PATENT DOCUMENTS

| | | | |
|---|---|---|---|
| 7,790,391 B2 | 9/2010 | Harris et al. | |
| 9,133,510 B2 * | 9/2015 | Andersen | C07H 21/00 |
| 9,957,552 B2 * | 5/2018 | Andersen | C07H 21/00 |
| 2008/0305481 A1 | 12/2008 | Whitman et al. | |
| 2010/0330574 A1 | 12/2010 | Whitman et al. | |
| 2011/0027790 A1 | 2/2011 | Harris et al. | |
| 2011/0045992 A1 | 2/2011 | Shao et al. | |
| 2013/0130917 A1 | 5/2013 | Cai | |

FOREIGN PATENT DOCUMENTS

| | | |
|---|---|---|
| EP | 2280080 A1 | 2/2011 |
| WO | 2008/121384 A1 | 10/2008 |
| WO | 2010/028366 A3 | 9/2009 |
| WO | 2010/028366 A2 | 3/2010 |

OTHER PUBLICATIONS

Aguirre De Carcer, Daniel, et al., "Evaluation of Subsampling-Based Normalization Strategies for Tagged High-Throughput Sequencing Data Sets from Gut Microbiomes", Applied and Environmental Microbiology, Dec. 15, 2011, 8795-8798.
Enroth, Stefan, et al., "A strand specific high resolution normalization method for chip-sequencing data employing multiple experimental control measurements", Algorithms for Molecular Biology, 7:2, 2012, 1-10.
EP17182486.5, Extended European Search Report dated Sep. 15, 2017, 11 pages.
Harris, Kirk, et al., "Comparison of Normalization Methods for Construction of Large, Multiplex Amplicon Pools for Next-Generation Sequencing", Applied and Environmental Microbiology, vol. 76, No. 12, 2010, 3863-3868.
Mamanova, Lira, et al., "Target-enrichment strategies for next generation sequencing", Nature Methods, vol. 7, No. 2, 2010, 111-118.
PCT/US2013/065108, International Preliminary Report on Patentability and Written Opinion dated Apr. 30, 2015, 7 Pages.
PCT/US2013/065108, International Search Report and Written Opinion dated Jan. 30, 2014, 11 pages.
Shearer, Aiden, et al., "Solution-based targeted genomic enrichment for precious DNA samples", BMC Biotechnology, 12:20, 2012, 1-6.
Singh, Pallavi, et al., "Target-Enrichment Through Amplification of Hairpin-Ligated Universal Targets for Next-Generation Sequencing Analysis", High-Throughput Next Generation Sequencing: Methods and Application, Methods in Molecular Biology, Chapter 19, vol. 733, 2011, 267-278.

\* cited by examiner

*Primary Examiner* — Young J Kim

(57) ABSTRACT

The present invention provides methods, compositions, kits, systems and apparatus that are useful for isolating nucleic acid molecules from a sample. In particular, the methods generally relate to normalizing the concentration of target nucleic acid molecules from a sample. In one aspect, the invention relates to purifying a primer extension product from a primer extension reaction mixture. In some aspects, nucleic acid molecules obtained using the disclosed methods, kits, systems and apparatuses can be used in various downstream processes including nucleic acid sequencing.

14 Claims, 3 Drawing Sheets

COMPOSITIONS, METHODS, SYSTEMS AND KITS FOR TARGET NUCLEIC ACID ENRICHMENT

CROSS REFERENCE TO RELATED APPLICATIONS

This application is a continuation of U.S. non-provisional application Ser. No. 14/829,297, filed Aug. 18, 2015, now U.S. Pat. No. 9,957,552, which is a divisional application of U.S. non-provisional application Ser. No. 14/054,618, filed Oct. 15, 2013, now U.S. Pat. No. 9,133,510, which claims benefit of priority under 35 U.S.C. § 119(e) to U.S. Provisional Application No. 61/714,206, filed Oct. 15, 2012 and U.S. Provisional Application No. 61/764,122 filed Feb. 13, 2013 entitled "COMPOSITIONS, METHODS, SYSTEMS AND KITS FOR TARGET NUCLEIC ACID ENRICHMENT", the disclosures of which are incorporated herein by reference in their entireties.

All literature and similar materials cited in this application, including but not limited to, patents, patent applications, articles, books, treatises, and internet web pages are expressly incorporated by reference in their entirety for any purpose.

TECHNICAL FIELD

In some embodiments, the present teachings provide compositions, systems, methods, apparatuses and kits for enrichment of target nucleic acid molecules from a sample or reaction mixture.

BACKGROUND

Sample preparation involving enrichment of target nucleic acid molecules from samples or reaction mixtures is frequently required prior to downstream applications such as cloning and nucleic acid sequencing. Typically, such downstream applications are performed in high throughput format, increasing the labor, time, and reagent costs for sample preparation prior to such techniques. Such applications frequently require the starting amounts and/or concentrations of nucleic acid molecule sample inputs to be normalized (or standardized) within an optimal working range. For example, many applications require normalization of nucleic acid samples before analysis can be performed, the purpose of such normalization being to substantially equalize the number of nucleic acid molecules (or concentration of nucleic acid molecules) within each sample to each other. These steps of quantification and normalization are extremely time-consuming and tedious; and strain laboratory resources as the number of target nucleic acid libraries to be quantified and/or normalized increases. Typically, to quantify a target nucleic acid library an aliquot of each sample is diluted and the nucleic acid concentration is determined. If the concentration of either or both samples varies significantly from the acceptable working range, the samples can be diluted or otherwise adjusted to acceptable starting amounts or concentrations. In some instances, the nucleic acid concentrations are adjusted to be substantially equal to each other during the normalization process. This process is referred to as "normalization" resulting in the generation of normalized samples having substantially equal numbers (or concentrations) of nucleic acid molecules. Such quantification and/or normalization processes, in addition to being labor-intensive, also impede the speed by which other downstream process can be initiated. In some instances, the time required to quantify and normalize several thousand target nucleic acid libraries can ultimately influence the speed by which sequencing data can be obtained from such downstream processes. Therefore, what is needed is an improved method for normalizing the starting number and/or concentration of nucleic acid molecules within one or more samples. What is also needed is a method by which to purify an extended primer product from a primer extension reaction mixture. Further, a method for isolating a specific amount of nucleic acid from a sample is desired.

SUMMARY

Figure 1:
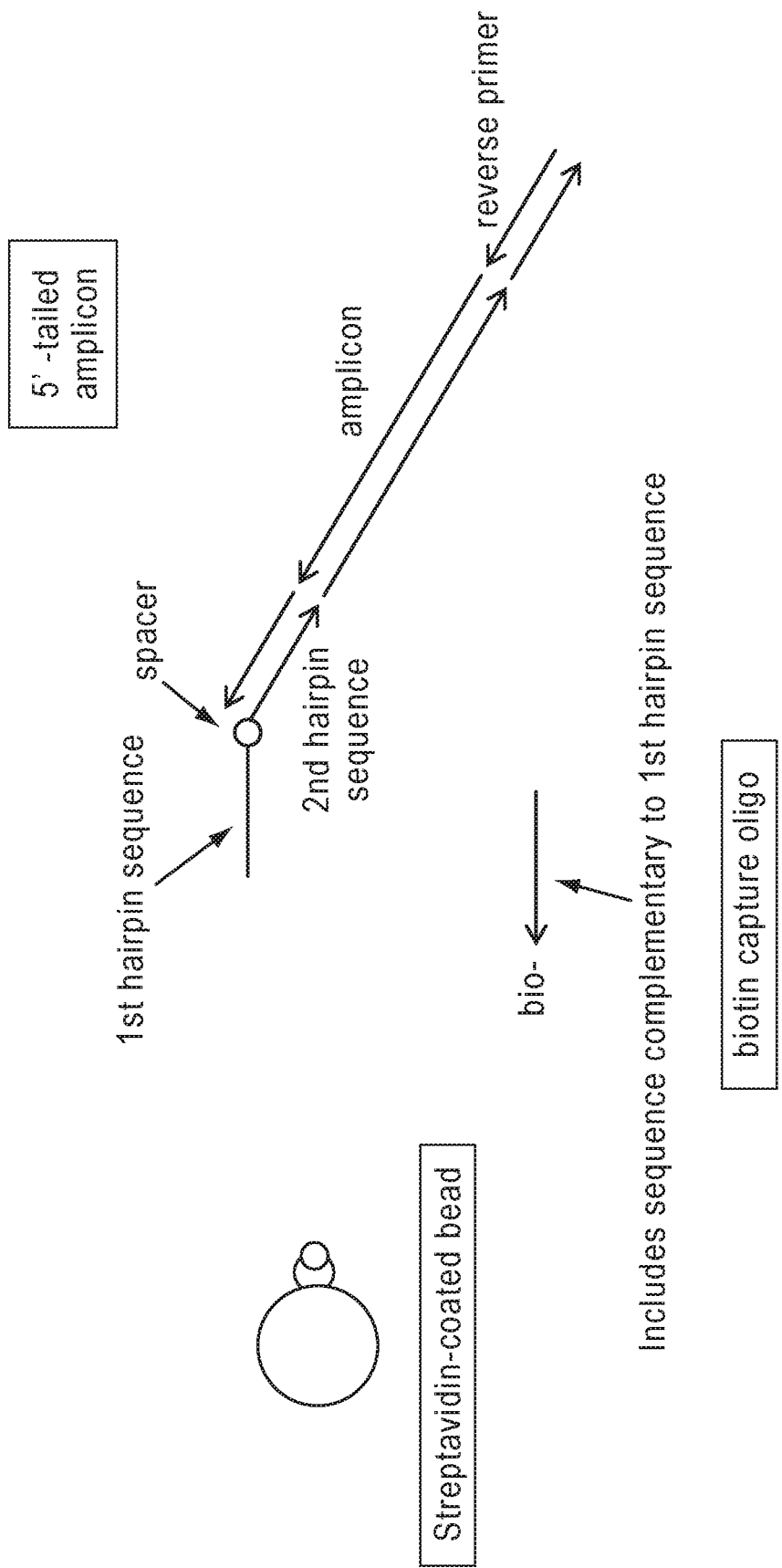
FIG. 1 is a schematic depicting a non-limiting embodiment of a target nucleic acid molecule enrichment method.

One particular exemplary application that can benefit from use of the target enrichment methods and normalization methods disclosed herein is nucleic acid sequencing, including next-generation sequencing (NGS). Many NGS platforms including the Ion Torrent Sequencers (Personal Genome Machine™ and Ion Torrent Proton™ Sequencers (Life Technologies, CA) require advance preparation and enrichment of large numbers of target nucleic acid molecules to be sequenced. Further details regarding the compositions, design and operation of the Ion Torrent PGM™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties. Various library preparation methods and kits exist within the NGS field that allow for the preparation of multiple target nucleic acid molecules from a single source (Ion Ampliseq™ Library Preparation, Publication Part Number: MAN0006735 or Ion Xpress™ Plus gDNA Fragment Library Preparation, Publication Part Number 4471989 (Life Technologies, CA); NEBNEXT® Fast DNA Library Prep Set for Ion Torrent, New England Biolabs Catalog # E6270L). The advent of barcoding has expanded this functionality by allowing the indexing of multiple target nucleic acid molecules from multiple samples or sources in a single sequencing run (Ion Xpress™ Barcode Adaptors 1-96 for use with Ion Xpress™ Plus Fragment Library Kit (Life Technologies, CA); Access Array™ Barcode Library, Fluidigm Corp, CA). Some areas of NGS, such as targeted re-sequencing, typically utilize many samples prepared in parallel, for example in several 96-well plates. The starting amounts of barcoded and non-barcoded nucleic acid libraries prepared using known library preparation methods vary widely and thus must be individually quantified before being transitioned into downstream processes. Quantification of target nucleic acid libraries can be achieved using a variety of protocols, including qPCR, Qubit® Fluorometer (Life Technologies, CA) and Bioanalyzer™ (Agilent Technologies, CA).

The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control.

It will be appreciated that there is an implied "about" prior to the temperatures, concentrations, times, etc discussed in the present teachings, such that slight and insubstantial deviations are within the scope of the present teachings herein.

Unless otherwise required by context, singular terms shall include pluralities and plural terms shall include the singular.

The use of "comprise", "comprises", "comprising", "contain", "contains", "containing", "include", "includes", and "including" are not intended to be limiting.

It is to be understood that both the foregoing general description and the following detailed description are exemplary and explanatory only and are not restrictive of the invention.

Unless otherwise defined, scientific and technical terms used in connection with the present teachings described herein shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with exemplary embodiments provided herein, the following terms, unless otherwise indicated, shall be understood to have the following meanings:

As used herein the term "amplification" and its variants includes any process for producing multiple copies or complements of at least some portion of a polynucleotide, said polynucleotide typically being referred to as a "template" or, in some cases, as a "target." The template (or target) polynucleotide can be single stranded or double stranded. Amplification of a given template can result in the generation of a population of polynucleotide amplification products, collectively referred to as an "amplicon".

As used herein, the term "sequencing" and its variants comprise obtaining sequence information from a nucleic acid strand, typically by determining the identity of at least one nucleotide (including its nucleobase component) within the nucleic acid strand. While in some embodiments, "sequencing" a given region of a nucleic acid molecule includes identifying each and every nucleotide within the region that is sequenced, "sequencing" can also include methods whereby the identity of one or more nucleotides in is determined, while the identity of some nucleotides remains undetermined or incorrectly determined.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The term "complementary" and its variants, as used herein in reference to two or more polynucleotides or nucleic acid sequences, refer to polynucleotides (or sequences within one or more polynucleoties) including any nucleic acid sequences that can undergo cumulative base pairing at two or more individual corresponding positions in antiparallel orientation, as in a hybridized duplex. Optionally there can be "complete" or "total" complementarity between a first and second nucleic acid sequence where each nucleotide in one of the nucleic acid sequences can undergo a stabilizing base pairing interaction with a nucleotide in the corresponding antiparallel position in the other nucleic acid sequence (however, the term "complementary" by itself can include nucleic acid sequences that include some noncomplementary portions, for example when one nucleic acid sequence is longer than the other). "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90% or 95%, but less than 100%, of the residues of one nucleic acid sequence are complementary to residues in the other nucleic acid sequence. Sequences are said to be "substantially complementary" when at least 80% of the residues of one nucleic acid sequence are complementary to residues in the other nucleic acid sequence. "Noncomplementary" describes nucleic acid sequences in which less than 20% of the residues of one nucleic acid sequence are complementary to residues in the other nucleic acid sequence. A "mismatch" is present at any position in the two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding between the nucleobases of nucleotides and/or polynucleotides at positions antiparallel to each other. The complementarity of other artificial base pairs can be based on other types of hydrogen bonding and/or hydrophobicity of bases and/or shape complementarity between bases.

The term "hybridize" or "anneal" and their variants, as used herein in reference to two or more polynucleotides, refer to any process whereby any one or more nucleic acid sequences (each sequence comprising a stretch of contiguous nucleotide residues) within said polynucleotides undergo base pairing at two or more individual corresponding positions, for example as in a hybridized nucleic acid duplex. Optionally there can be "complete" or "total" hybridization between a first and second nucleic acid sequence, where each nucleotide residue in the first nucleic acid sequence can undergo a base pairing interaction with a corresponding nucleotide in the antiparallel position on the second nucleic acid sequence. In some embodiments, hybridization can include base pairing between two or more nucleic acid sequences that are not completely complementary, or are not base paired, over their entire length. For example, "partial" hybridization occurs when two nucleic acid sequences undergo base pairing, where at least 20% but less than 100%, of the residues of one nucleic acid sequence are base paired to residues in the other nucleic acid sequence. In some embodiments, hybridization includes base pairing between two nucleic acid sequences, where at least 50%, but less than 100%, of the residues of one nucleic acid sequence are base paired with corresponding residues in the other nucleic acid sequence. In some embodiments, at least 70%, 80%, 90% or 95%, but less than 100%, of the residues of one nucleic acid sequence are base paired with corresponding residues in the other nucleic acid sequence. Two nucleic acid sequences are said to be "substantially hybridized" when at least 85% of the residues of one nucleic acid sequence are base paired with corresponding residues in the other nucleic acid sequence. In situations where one nucleic acid molecule is substantially longer than the other (or where the two nucleic acid molecule include both substantially complementary and substantially non-complementary regions), the two nucleic acid molecules can be described as "hybridized" even when portions of either or both nucleic acid molecule can remain unhybridized. "Unhybridized" describes nucleic acid sequences in which less than 20% of the residues of one nucleic acid sequence are base paired to residues in the other nucleic acid sequence. In some embodiments, base pairing can occur according to some conventional pairing paradigm, such as the A-T/U and G-C base pairs formed through specific Watson-Crick type hydrogen bonding between the nucleobases of nucleotides and/or polynucleotides positions antiparallel to each other; in other embodiments, base pairing can occur through any other paradigm whereby base pairing proceeds according to established and predictable rules.

Hybridization of two or more polynucleotides can occur whenever said two or more polynucleotides come into contact under suitable hybridizing conditions. Hybridizing conditions include any conditions that are suitable for nucleic acid hybridization; methods of performing hybridization and suitable conditions for hybridization are well known in the art. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "$T_m$"; parameters such as salts, buffers, pH, temperature, GC % content of the polynucleotide and primers, and/or time. Typically, hybridization is favored in lower temperatures and/or increased salt concentrations, as well as reduced concentrations of organic solvents. High-stringency hybridization conditions will typically require a higher degree of complementary between two target sequences for hybridization to occur, whereas low-stringency hybridization conditions will favor hybridization even when the two polynucleotides to be hybridized exhibit lower levels of complementarity. The hybridization conditions can be applied during a hybridization step, or an optional and successive wash step, or both the hybridization and optional wash steps.

Examples of high-stringency hybridization conditions include any one or more of the following: salt concentrations (e.g., NaCl) of from about 0.0165 to about 0.0330 M; temperatures of from about 5° C. to about 10° C. below the melting point ($T_m$) of the target sequences (or polynucleotides) to be hybridized; and/or formamide concentrations of about 50% or higher. Typically, high-stringency hybridization conditions permit binding between sequences having high homology, e.g., ≥95% identity or complementarity. In one exemplary embodiment of high-stringency hybridization conditions, hybridization is performed at about 42° C. in a hybridization solution containing 25 mM $KPO_4$ (pH 7.4), 5×SSC, 5×Denhardt's solution, 50 µg/mL denatured, sonicated salmon sperm DNA, 50% formamide, 10% Dextran sulfate, and 1-15 ng/mL double stranded polynucleotide (or double stranded target sequence), while the washes are performed at about 65° C. with a wash solution containing 0.2×SSC and 0.1% sodium dodecyl sulfate.

Examples of medium-stringency hybridization conditions can include any one or more of the following: salt concentrations (e.g., NaCl) of from about 0.165 to about 0.330 M; temperatures of from about 20° C. to about 29° C. below the melting point ($T_m$) of the target sequences to be hybridized; and/or formamide concentrations of about 35% or lower. Typically, such medium-stringency conditions permit binding between sequences having high or moderate homology, e.g., ≥80% identity or complementarity. In one exemplary embodiment of medium stringency hybridization conditions, hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL double stranded polynucleotide (or double stranded target sequence), while the washes are performed at about 50° C. with a wash solution containing 2×SSC and 0.1% sodium dodecyl sulfate.

Examples of low-stringency hybridization conditions include any one or more of the following: salt concentrations (e.g., NaCl) of from about 0.330 to about 0.825 M; temperatures of from about 40° C. to about 48° C. below the melting point ($T_m$) of the target sequences to be hybridized; and/or formamide concentrations of about 25% or lower. Typically, such low-stringency conditions permit binding between sequences having low homology, e.g., ≥50% identity or complementarity.

Some exemplary conditions suitable for hybridization include incubation of the polynucleotides to be hybridized in solutions having sodium salts, such as NaCl, sodium citrate and/or sodium phosphate. In some embodiments, hybridization or wash solutions can include about 10-75% formamide and/or about 0.01-0.7% sodium dodecyl sulfate (SDS). In some embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In some embodiments, the hybridization or washing solution can include BSA (bovine serum albumin). In some embodiments, hybridization or washing can be conducted at a temperature range of about 20-25° C., or about 25-30° C., or about 30-35° C., or about 35-40° C., or about 40-45° C., or about 45-50° C., or about 50-55° C., or higher.

In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer.

In some embodiments, hybridization or wash conditions can be conducted at a pH range of about 5-10, or about pH 6-9, or about pH 6.5-8, or about pH 6.5-7.

As used herein, the terms "melting temperature" and "$T_m$" and their variants, when used in reference to a given polynucleotide (or a given target sequence within a polynucleotide) typically refers to a temperature at which 50% of the given polynucleotide (or given target sequence) exists in double-stranded form and 50% is single stranded, under a defined set of conditions. In some embodiments, the defined set of conditions can include a defined parameter indicating ionic strength and/or pH in an aqueous reaction condition. A defined condition can be modulated by altering the concentration of salts (e.g., sodium), temperature, pH, buffers, and/or formamide. Typically, the calculated thermal melting temperature can be at about 5-30° C. below the $T_m$, or about 5-25° C. below the $T_m$, or about 5-20° C. below the $T_m$, or about 5-15° C. below the $T_m$, or about 5-10° C. below the $T_m$. The Tm of a given nucleic acid sequence can be calculated according to any suitable method (including both actual melting assays as well as $T_m$ prediction algorithms) as long as comparisons of $T_m$ values are performed using $T_m$ values obtained using the same calculation methods. Methods for calculating a $T_m$ are well known and can be found in Sambrook (1989 in "Molecular Cloning: A Laboratory Manual", $2^{nd}$ edition, volumes 1-3; Wetmur 1966, J. Mol. Biol., 31:349-370; Wetmur 1991 Critical Reviews in Biochemistry and Molecular Biology, 26:227-259). Other sources for calculating a $T_m$ for hybridizing or denaturing nucleic acids include OligoAnalyze (from Integrated DNA Technologies), OligoCalc and Primer3 (distributed by the Whitehead Institute for Biomedical Research). In some embodiments of the methods provided herein, the $T_m$ of a given nucleic acid sequence is calculated according to any one or more of these methods. In some embodiments, the $T_m$ is calculated assuming the following conditions nucleic acid sequence is suspended in a solution including 50 nM of nucleic acid sequence in a Tris-based buffer including 50 nM salt (e.g., NaCl). In some embodiments, the Tm is calculated assuming 50 nM nucleic acid sequence in a solution including 0.5M NaCl. In some embodiments, the Tm is calculated assuming that the nucleic acid sequence is present at a concentration of 100 pM in a buffer containing: 10 mM Tris pH 8.0; 500 mM NaCl; 0.1 mM EDTA and 0.05% Tween-20.

As used herein, the term "primer" and its variants can include any single stranded nucleic acid molecule (regardless of length) that, once hybridized to a complementary nucleic acid sequence, can prime nucleic acid synthesis. Typically, such nucleic acid synthesis occurs in a template-dependent fashion, and nucleotides are polymerized onto at least one end of the primer during such nucleic acid synthesis. The term "primer extension" and its variants, as used herein, when used in reference to a given method, relates to any method for catalyzing nucleotide incorporation onto a terminal end of a nucleic acid molecule. Typically but not necessarily such nucleotide incorporation occurs in a template-dependent fashion. In some embodiments, the primer extension activity of a given polymerase can be quantified as the total number of nucleotides incorporated (as measured by, e.g., radiometric or other suitable assay) by a unit amount of polymerase (in moles) per unit time (seconds) under a particular set of reaction conditions.

As used herein, the term "hairpin", when used in reference to any oligonucleotide, printer, polynucleotide or nucleic acid molecule, refers to an oligonucleotide, primer, polynucleotide or nucleic acid molecule that includes two nucleic acid sequences (referred to herein as a "first hairpin sequence" and a "second hairpin sequence" that are at least 70% complementary to each other. In some embodiments, the first and second hairpin sequences are at least 75%, 77%, 80%, 85%, 90%, 95%, 97%, 99% complementary to each other, or are completely complementary. The first and second hairpin sequences are optionally capable of hybridizing to each other under suitable conditions. The hybrid formed via hybridization of first and second hairpin sequences to each other can have a melting temperature ($T_m$) referred to as "the hairpin melting temperature" or "the hairpin $T_m$". Typically, the first and second hairpin sequences are in reverse orientation with respect to each other, such that hybridization of the first and second hairpin sequences will result in the formation of a hairpin structure at temperatures below the hairpin $T_m$. In some embodiments, the hairpin oligonucleotide, primer, polynucleotide or nucleic acid molecule exists predominantly in the hairpin form at temperatures significantly below the hairpin melting temperature, and predominantly in the extended (melted) single-stranded form at temperatures significantly above the hairpin melting temperature. The first and second hairpin sequences can be of any length, but are typically greater than 4 nucleotides long, even more typically greater than about 5, 6, 7, 8, 9, 10, 11, 12, 13, 14, 15, 20, 25, 50, 75 or 100 nucleotides long. In some embodiments, the melting temperature (Tm) of the first and second sequences is lower than about 80° C., or lower than about 70° C., or lower than about 65° C., or lower than about 60° C., or lower than about 55° C. when measured under standard PCR extension conditions.

As used herein, the term "nucleotide" and its variants comprise any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. Some examples of nucleotide analogs are described in Xu, U.S. Pat. No. 7,405,281. In some embodiments, the nucleotide comprises a label (e.g., reporter moiety) and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group or substitute phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprise polymerization of one or more nucleotides to form a nucleic acid strand including at least two nucleotides linked to each other, typically but not necessarily via phosphodiester bonds, although alternative linkages may be possible in the context of particular nucleotide analogs.

The terms "oligonucleotide", "polynucleotide" "nucleic acid molecule" and their variants, as used herein, can be used interchangeably to refer to any polymers that include one or more polynucleotide regions, without regard to the respective lengths of such polymers. In some embodiments, such polymers can include non-polynucleotide regions as well. Such polymers have at least 2 ends, which for sake of convenience may be referred to herein as the 5' and the 3' end, although such terminology does not limit the structure of the underlying ends. For example, a 3' end of a primer, oligonucleotide, polynucleotide or nucleic acid molecule does not necessarily include a free hydroxyl group and instead can include any other chemical group that can interact or react with an incoming nucleotide during a nucleotide incorporation reaction. Unless made otherwise clear by the context, such oligonucleotide, polynucleotide or nucleic acid molecule can be double stranded or single stranded. While in some embodiments, the oligonucleotide (or primer) is shorter than a corresponding polynucleotide template (or template nucleic acid molecule), in some embodiments the oligonucleotide or primer will not be shorter than a corresponding polynucleotide template (or template nucleic acid molecule).

As used herein, the term "adaptor" includes polynucleotides or oligonucleotides comprising DNA, RNA, chimeric RNA/DNA molecules, or analogs thereof. In some embodiments, an adaptor can include one or more ribonucleoside residues. In some embodiments, an adaptor can be single-stranded or double-stranded nucleic acids, or can include single-stranded and/or double-stranded portions. In some embodiments, an adaptor can have any structure, including linear, hairpin, forked, or stem-loop.

In some embodiments, an adaptor can have any length, including fewer than 10 bases in length, or about 10-20 bases in length, or about 20-50 bases in length, or about 50-100 bases in length, or longer.

In some embodiments, an adaptor can have any combination of blunt end(s) and/or sticky end(s). In some embodiments, at least one end of an adaptor can be compatible with at least one end of a nucleic acid fragment. In some embodiments, a compatible end of an adaptor can be joined to a compatible end of a nucleic acid fragment. In some embodiments, an adaptor can have a 5' or 3' overhang end.

In some embodiments, an adaptor can have a 5' or 3' overhang tail. In some embodiments, the tail can be any length, including 1-50 or more nucleotides in length.

In some embodiments, an adaptor can include an internal nick. In some embodiments, an adaptor can have at least one strand that lacks a terminal 5' phosphate residue. In some embodiments, an adaptor lacking a terminal 5' phosphate residue can be joined to a nucleic acid fragment to introduce a nick at the junction between the adaptor and the nucleic acid fragment.

In some embodiments, an adaptor can include a nucleotide sequence that is part of, or is complementary to, any portion of a primer, or to the entire sequence of a primer, present in the amplification reaction mixture, or any portion of a sequencing primer, or the entire sequence of a sequencing primer, or any portion thereof.

In some embodiments, an adaptor can include degenerate sequences. In some embodiments, an adaptor can include one or more inosine residues. In some embodiments, a barcode adaptor can include a uniquely identifiable sequence. In some embodiments, a barcode adaptor can be used for constructing multiplex nucleic acid libraries.

In some embodiments, an adaptor can include at least one scissile linkage. In some embodiments, a scissile linkage can be susceptible to cleavage or degradation by an enzyme or chemical compound. In some embodiments, an adaptor can include at least one phosphorothiolate, phosphorothioate, and/or phosphoramidate linkage.

In some embodiments, an adaptor can include identification sequences. In some embodiments, an identification sequences can be used for sorting or tracking. In some embodiments, an identification sequences can be a unique sequence (e.g., barcode sequence). In some embodiments, a barcode sequence can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences.

In some embodiments, an adaptor can include any type of restriction enzyme recognition sequence, including type I, type II, type Hs, type IIB, type III or type IV restriction enzyme recognition sequences.

In some embodiments, an adaptor can include a cell regulation sequences, including a promoter (inducible or constitutive), enhancers, transcription or translation initiation sequence, transcription or translation termination sequence, secretion signals, Kozak sequence, cellular protein binding sequence, and the like.

In some embodiments, the term "substantially equal" and its variants, when used in reference to two or more values, refers to any two or more values that are less than 10 times each other, typically less than 5 times, even more typically less than 3 times of any other value, even more typically no greater than 2 times each other. For example, for purposes of the present disclosure, values of 1 and 9 can be considered to be substantially equal, but not values of 1 and 20. In some embodiments, the term "substantially equal" is used to refer to two or more output values each indicating a number of molecules or a final concentration of molecules derived from a sample. In some embodiments, "substantially equal" refers to an output nucleic acid concentration of target nucleic acid molecules isolated from two or more samples; for example, output concentrations of nucleic acid molecules recovered from a first and second sample are said to be "substantially equal" if the output concentration from the first sample is less than 10 times the output concentration from the second sample. In some embodiments, "substantially equal" includes any output nucleic acid concentrations from two or more sample that are within one standard deviation of each other. In some embodiments, "substantially equal" refers to the absolute number of nucleic acid molecules isolated from two or more samples. In some embodiments, a first number of target nucleic acid molecules is isolated from a first sample, and a second number of target nucleic acid molecules is isolated from a second sample, where the first number varies by no more than 5%, 10%, 15%, 20%, 25%, 50%, 75%, 100%, 200%, 250%, 500%, 750%, 900%, or 990% from the second number, or vice versa. In some embodiments, "substantially equal" refers to the concentration of nucleic acid molecules isolated from two or more samples, wherein the concentration of nucleic acid molecules between the two or more samples varies by less than 5 times, more preferably by less than 3 times, even more typically no greater than 2 times of each other. In some embodiments, "substantially equal" refers to the number or concentration of nucleic acid molecules in a second sample, that is within about 1%, 2%, 3%, 4%, 5%, 10%, 15%, 20%, 25%, 30%, 35% or 40% of the mean concentration or mean number of nucleic acid molecules in a first sample. In some embodiments, a substantially equal output nucleic acid concentration can include any concentration of from about 1 pM to about 1000 pM, for example about 10 pM, 20 pM, 40 pM, 50 pM, 60 pM, 70 pM, 80 pM, 100 pM, 200 pM, 300 pM, 400 pM, 500 pM, 600 pM, 700 pM, 800 pM, 900 pM or more. In some embodiments, substantially equal outputs can include any outputs' within a range of about 2-fold, 3-fold, 4-fold or 5-fold.

As used herein, the term "binding partners" includes two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions.

In some embodiments, molecules that function as binding partners include: biotin (and its derivatives) and their binding partner avidin moieties, streptavidin moieties (and their derivatives); His-tags which bind with nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

An avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g. nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin™, Captavidin™, Neutravidin™ and Neutralite Avidin™.

In some embodiments, the disclosure relates generally to methods for isolating target nucleic acid molecules using a capture moiety, as well as related compositions, kits, systems and apparatuses. In some embodiments, the methods (and relating compositions, systems, apparatuses and kits) can involve contacting a sample including a population of target nucleic acid molecules with first number of molecules of a capture oligonucleotide. In some embodiments, the capture oligonucleotide is capable of selectively binding to any one, some or all members of the population of target nucleic acid molecules; such selective binding optionally includes sequence-specific hybridization between a sequence of the capture oligonucleotide and a sequence of the target nucleic acid molecules of the population. In some embodiments (and in contrast to many conventional methods of target enrichment using capture oligonucleotides), the first number of capture oligonucleotide molecules that are contacted with the target nucleic acid molecules can be a limiting number. By "limiting" it is meant that the number of molecules of capture oligonucleotide is significantly less than the number of target nucleic acid molecules within the sample that are capable of binding to the capture oligonucleotide. (Such embodiments contrast with many conventional methods of enrichment for target nucleic acid molecules using capture oligonucleotides, where the amount/number of capture oligonucleotide is typically in excess relative to target). Optionally, the first number of capture oligonucleotide molecules is less than 50%, 25%, 10% or 1% of the number of target nucleic acid molecules in the sample that are capable of binding to the capture oligonucleotide.

In some embodiments, the capture oligonucleotide binds selectively (e.g., via sequence-specific hybridization) to at least some of the target nucleic acid molecules in the sample, creating a population of bound target nucleic acid molecules. In some embodiments, the methods further include capturing at least some of the bound target nucleic acid molecules using an agent that selectively binds to the capture oligonucleotide, creating a population of captured target nucleic acid molecules. In some embodiments, the number of captured target nucleic acid molecules in the population of captured target nucleic acid molecules is directly proportional to the first number of capture oligonucleotide molecules. This feature can allow the recovery of substantially equal numbers of captured target nucleic acid molecules from multiple samples in parallel, without the need for individually measuring the concentration of such samples.

In some embodiments, the capture oligonucleotide includes a capture moiety that selectively binds to the binding agent. For example, the capture moiety can include a first member of a binding pair, and the binding agent can include a second member of the same binding pair. In some embodiments, the capture oligonucleotide includes a biotin capture moiety, and the binding agent is a streptavidin-containing support.

In some embodiments, the disclosure relates generally to methods (and related compositions, systems, apparatuses and kits) for isolating a specific amount of nucleic acid from a sample, comprising: generating a population of bound target nucleic acid molecules by contacting a sample including a population of target nucleic acid molecules with a limiting number of capture oligonucleotides under conditions where at least some of the capture oligonucleotides hybridize to at least some of the target nucleic acid molecules. Optionally, the methods further include forming a population of captured target nucleic acid molecules by capturing a substantial portion of the population of bound target nucleic acid molecules, wherein the number of captured target nucleic acid molecules is directly proportional to the limiting number of capture oligonucleotides.

In some embodiments, the disclosure relates generally to a method for normalizing the concentration of two or more nucleic acid samples, comprising: forming a first population of captured target nucleic acid molecules from a first sample according to the methods disclosed herein, and forming a second population of captured target nucleic acid molecules from a second sample according to the same method, wherein the number of captured target nucleic acid molecules in the first and second populations of captured target nucleic acid molecules vary no greater than 5 fold from each other. In some embodiments, the number of captured target nucleic acid molecules in the first and second populations of captured target nucleic acid molecules varies within a range of about 2-fold, 3-fold, or 4-fold.

In some embodiments, the capture oligonucleotide includes a capture sequence that is substantially complementary to a corresponding capture sequence within the target nucleic acid molecule. The Tm of the hybrid formed between the capture sequences of the capture oligonucleotide and the target nucleic acid molecule (referred to herein as "the capture Tm") can be less than about 50° C., 45° C., 40° C., 35° C., 30° C., 25° C., 20° C., or lower.

In some embodiments, the method can further include use of a capture oligonucleotide which can capture or hybridize to the target nucleic acid molecules at permissive conditions, but which does not significantly capture or hybridize to the target nucleic acid molecules at non-permissive conditions. The permissive conditions can include, for example, lower temperatures (e.g., temperatures significantly below the capture Tm), high salt (e.g., NaCl concentrations of 0.25M, 0.3M, 0.4M, 0.5M, 0.75M, 1M or higher), low or absent levels of denaturing chemicals, etc. The non-permissive conditions can include, for example, higher temperatures (e.g., temperatures significantly above the capture Tm), low or absent levels of salt (e.g., NaCl concentrations of 0.2M, 0.1M, 0.05M, 0.001M, or low), low or absent levels of denaturing chemicals, etc.

In some embodiments, the disclosed methods can include hybridizing a population of target nucleic acid molecules in a sample with a limiting number of capture oligonucleotides at permissive conditions to form a population of bound target nucleic acid molecules, capturing the bound target molecules by capturing the bound target nucleic acid molecules with a binding agent to form a population of captured target nucleic acid molecules, and then subjecting the captured nucleic acid molecules to non-permissive conditions to elute the captured nucleic acid molecules from the binding agent, thereby forming a population of eluted target nucleic acid molecules. The number of eluted target nucleic acid molecules is directly proportional to the limiting number of capture oligonucleotides used in the hybridizing step. In some embodiments, multiple samples are processed in parallel in this manner using the same number of capture oligonucleotides with each sample, and the method further includes recovering substantially equal numbers or concentrations of eluted target nucleic acid molecules from each sample.

In embodiments involving purification of primer extension products (including primer extension products formed via amplification processes such as PCR), it can be desirable to avoid unintended capture of unextended primers by the capture oligonucleotide though use of a hairpin oligonucleotide (also referred to herein as "a hairpin primer") to drive primer extension. Accordingly, in some embodiments, the disclosure relates generally to compositions for isolating primer extension products, comprising a hairpin oligonucleotide having a first hairpin sequence and a second hairpin sequence. In some embodiments, the first and/or second hairpin sequences are each independently between 3 and 100 nucleotides long, for example between 5 and 20 nucleotides long. In some embodiments, the hairpin oligonucleotide includes a first hairpin sequence that is substantially or completely complementary to a second hairpin sequence within the hairpin oligonucleotide. The Tm of the hybrid formed between the first and second hairpin sequences (referred to herein as "the hairpin Tm") can be less than about 50° C., 45° C., 40° C., 35° C., 30° C., 25° C., 20° C., or lower.

In some embodiments, the hairpin primer will exist predominantly in hybridized or hairpin form at permissive conditions, and predominantly in linear or denatured form at non-permissive conditions. The permissive conditions can include, for example, lower temperatures (e.g., temperatures significantly below the hairpin Tm), high salt (e.g., NaCl concentrations of 0.25M, 0.3M, 0.4M, 0.5M, 0.75M, 1M or higher), low or absent levels of denaturing chemicals, etc. The non-permissive conditions can include, for example, higher temperatures (e.g., temperatures significantly above the hairpin Tm), low or absent levels of salt (e.g., NaCl concentrations of 0.2M, 0.1M, 0.05M, 0.001M, or low), low or absent levels of denaturing chemicals, etc. In some embodiments, the method can include a permissive condition for hairpin formation and a non-permissive condition for capture target hybridization. In some embodiments, the method can include a non-permissive condition for hairpin formation and a permissive condition for capture-target hybridization. In some embodiments, the method can include permissive conditions for both hairpin formation and capture target hybridization. In some embodiments, the method can include non-permissive conditions for both hairpin formation and capture target hybridization.

In some embodiments, the disclosed methods can include hybridizing a population of target nucleic acid molecules in a sample with the hairpin primer at nonpermissive conditions to form a population of hairpin primer-target complexes, and extending the hairpin primer in a template-dependent fashion to form a hairpin primer extension product. In some embodiments, the method can further include subjecting the primer extension mixture to permissive conditions to induce the formation of hairpins by substantially all of the unextended hairpin primers. This ensures that the unextended hairpin primers do not significantly (or substantially) bind to the capture oligonucleotide during the subsequent capture step.

Optionally, the first and second hairpin sequences of the hairpin primer are separated by a spacer region. The spacer region can optionally include one or more nucleotides or can be comprised entirely of non-nucleotidyl moieties. In some embodiments, the spacer region includes a non-replicable moiety that cannot be replicated by a polymerase. Such non-replicable moieties can include any moiety that cannot support template-based nucleotide polymerization by a polymerase. For example, the non-replicable moiety can include a non-nucleotidyl moiety (e.g., PEG or other carbon-based spacer, amino acid, or nucleotide analog that is not recognized by the polymerase used to perform the primer extension, for example uracil in conjunction with a DNA-dependent DNA polymerase, etc). When the hairpin primer is used as a template for template-dependent nucleic acid synthesis by a polymerase, the polymerase cannot extend the synthesized nucleic acid strand beyond the non-replicable moiety. This typically results in the cessation or termination of nucleic acid synthesis after some portion of the hairpin oligonucleotide has been copied into an opposing strand, leaving the remaining portion of the hairpin oligonucleotide single stranded. The synthesized or replicated strand can remain base paired to the hairpin oligonucleotide, forming a hairpin primer extension product that is partly double stranded and partly single stranded. The single stranded region optionally includes some portion of the hairpin primer.

In some embodiments, the single stranded region of the hairpin primer extension product includes a capture sequence that can bind to a corresponding capture sequence in the capture oligonucleotide. Optionally, the capture sequence of the hairpin oligonucleotide is at least 70% complementary to the capture sequence of the capture oligonucleotide. In some embodiments, the capture sequence of the hairpin oligonucleotide and capture oligonucleotides are completely complementary to each other.

In some embodiments, the hairpin oligonucleotide is predominantly single stranded at temperatures significantly above the hairpin melting temperature ("hairpin Tm"). At temperatures significantly below the hairpin melting temperature ("hairpin Tm"), the hairpin form of the oligonucleotide predominates.

Optionally, the composition further includes a target nucleic acid molecule. The target nucleic acid molecule can include a sequence that is at least partially complementary to a sequence of the hairpin.

Optionally, the composition further includes a capture oligonucleotide.

In some embodiments, the target nucleic acid molecule can include a sequence that is at least partially complementary to a sequence of the hairpin.

In some embodiments, the target nucleic acid molecule and the capture oligonucleotide each separately include a sequence that is at least partially complementary to the first and/or second hairpin sequences.

In some embodiments, the capture Tm can be selected to allow hybridization of the two capture sequences at permissive conditions, where the two capture sequences are denatured under non-permissive conditions. The permissive conditions can include any temperature significantly below the capture Tm (e.g., room temperature or below). In some embodiments, the permissive conditions include high salt concentrations (e.g., NaCl of 0.1M or higher, typically 0.25M, even more typically 0.5M or higher). Following capture at permissive conditions, the captured product can optionally be washed to remove non-specifically bound contaminants. The purified primer extension product can then be eluted from the capture oligonucleotide via exposure to non-permissive conditions (e.g., temperature significantly above capture Tm and/or low salt concentrations). Since the amount of capture oligonucleotide used to perform the capture is limiting, the amount of purified primer extension product will be directly proportional to the number of capture oligonucleotide molecules used to perform the capture. When such capture is performed on multiple samples in parallel using the same number of capture oligonucleotides, the number of purified product molecules obtained from each sample should be directly proportional to the number of capture oligonucleotide molecules used in the assay. In some embodiments, the number of purified product molecules recovered from each sample are substantially equal to each other.

In some embodiments, the disclosure relates generally to kits for normalization of nucleic acid samples, comprising: a container including a hairpin oligonucleotide. The hairpin oligonucleotide can include any hairpin oligonucleotide disclosed herein. In some embodiments, the kit further includes the same container (or a different container) including a capture oligonucleotide. Optionally, the hairpin oligonucleotide includes a capture sequence that is at least 85% complementary to a sequence of the capture oligonucleotide.

In some embodiments, the disclosure relates generally to methods (and related compositions, kits, systems and apparatuses) for purifying a primer extension product from a primer extension reaction mixture, comprising: hybridizing a hairpin primer to a target nucleic acid (or to a population of target nucleic acid molecules) within a sample. Optionally, the hairpin primer includes a first hairpin sequence and a second hairpin sequence. The first and second hairpin sequences can be substantially or completely complementary to each other. The Tm of the hybrid formed between the first and second hairpin sequences ("hairpin Tm") can be about 50° C. or lower. The method can optionally include forming a primer extension reaction mixture including a hairpin primer and one or more target nucleic acid molecules. The method can include hybridizing the hairpin primer to one or more target nucleic acid molecules of the sample at a nonpermissive temperature at which substantially all (or a significant portion) of the hairpin primers are in linear or extended form. In some embodiments, the method further includes extending the hairpin primer in a target-dependent fashion at a permissive condition to form one or more extended hairpin primer products. In some embodiments, the method further includes subjecting the primer extension reaction mixture including the one or more extended primer products to nonpermissive conditions such that substantially all (or a significant portion) of unextended hairpin primers are in the hairpin form. The method can further include contacting the extended hairpin primers with a capture oligonucleotide under conditions permitting hybridization of the capture oligonucleotide to the extended hairpin primers. In some embodiments, the extended hairpin primers are partly double stranded and partly single stranded, and the capture oligonucleotide hybridizes to a sequence within the single stranded portion of the extended hairpin primers.

In some embodiments, the disclosure relates generally to a method (and related compositions and kits) for purifying a primer extension product from a primer extension reaction mixture, comprising: hybridizing a hairpin primer to one or more target nucleic acid molecules. Optionally, the hairpin primer includes a first hairpin sequence and a second hairpin sequence separated by a non-replicable moiety. In some embodiments, the first and second hairpin sequences can be separated by a non-replicable moiety. In some embodiments, the method further includes extending the hairpin primer in a template-dependent fashion to form a hairpin primer extension product having a single stranded region including the first hairpin sequence.

In some embodiments, the method further includes hybridizing the hairpin primer extension product to a capture oligonucleotide that includes a capture moiety.

In some embodiments, the method further includes selectively capturing the hairpin primer extension product using a binding agent that selectively binds to the capture moiety.

In some embodiments, the capture oligonucleotide includes a sequence that is substantially complementary to at least a portion of the single stranded region of the hairpin primer extension product.

In some embodiments, the capture oligonucleotide includes a sequence that is substantially complementary to at least a portion of the first hairpin sequence.

In some embodiments, the extending is performed at a temperature ("extension temperature") that is significantly above the hairpin Tm, such that the first and second hairpin sequences of the hairpin primer do not substantially hybridize to each other at the extension temperature.

In some embodiments, the primer extension product is hybridized to the capture oligonucleotide at a temperature ("capture temperature") significantly below the hairpin Tm, such that substantially all unextended hairpin oligonucleotide is in the hairpin form at the capture temperature.

In some embodiments, the disclosure relates generally to kits for isolating target nucleic acid molecules using a capture oligonucleotide, as well as related compositions, methods, systems and apparatuses. In some embodiments, the kits (and relating compositions, systems, apparatuses and methods) include a capture oligonucleotide capable of selectively binding to one or some portion of members of a population of target nucleic acid molecules. In some embodiments, the kit can optionally include the capture oligonucleotide in a limited amount or amount that can be diluted so as to be present in a limiting number, compared to the population of target nucleic acid molecules that can selectively bind to the capture oligonucleotide. In some embodiments, the capture oligonucleotide can be present in an amount less than 50%, 25%, 20%, 10%, 5% or 1% of the number of target nucleic acid molecules in the sample capable of binding to the capture oligonucleotide. In some embodiments, the capture oligonucleotide includes a capture moiety that selectively binds to a binding agent. For example, the capture moiety can include a first member of a binding pair, and the binding agent can include a second member if the same binding pair. In some embodiments, the kit can further include one or more hairpin primers. The hairpin primers can include any hairpin primer disclosed herein. In some embodiments, the hairpin primer includes a first hairpin sequence and a second hairpin sequence that are complementary to each other and will hybridize to each other (forming a hairpin structure) at temperatures significantly below the hairpin Tm. Optionally, the kit can further include a binding agent that selectively binds to the capture oligonucleotide.

EXAMPLES

FIG. 1 depicts an exemplary embodiment of a normalization method as described in Example 1, wherein a target nucleic acid molecule is amplified using a hairpin primer (for forward strand synthesis) and a reverse primer (for reverse strand synthesis) using PCR. The hairpin primer includes a first hairpin sequence and a second hairpin sequence that are complementary to each other and will hybridize to each other at permissive temperatures (e.g., temperatures significantly below the hairpin Tm) and/or at permissive salt concentrations. The hairpin primer also includes a non-replicable spacer comprising a carbon-18 (C18) spacer. The amplification product includes the hairpin oligonucleotide, part of which remains single stranded. The single stranded region of the amplification product includes a capture sequence, which is complementary to a corresponding capture sequence on a biotinylated capture oligonucleotide. The capture sequence has an estimated Tm of about 36° C. in 50 mM NaCl. The amplified product is captured by hybridization to a limiting amount of capture oligonucleotide (133 pM in 75 ul) at permissive temperatures (e.g., room temperature or lower) and/or permissive salt concentrations (e.g., 0.5M NaCl or greater). The capture oligonucleotide-product complex can then be selectively captured using the binding agent streptavidin, e.g., via mixture with streptavidin-coated beads. The beads containing the captured product can be washed to remove non-specifically bound material. The captured amplified product can be eluted from the beads by using an elution solution including non-permissive (low) salt concentrations and/or exposure to non-permissive (elevated) temperatures to denature the hybridization product between the capture sequence of the capture oligonucleotide and the capture sequence of the single stranded portion of the amplified product.

The target enrichment methods disclosed herein can be advantageously used to simplify the workflow and reduce the cost and effort of preparing large numbers of samples for analysis by allowing the preparation of large numbers of nucleic acid samples containing substantially equal numbers (or concentrations) of nucleic acid molecules.

Example 1: Library Normalization by Limiting Capture

Figure 2:
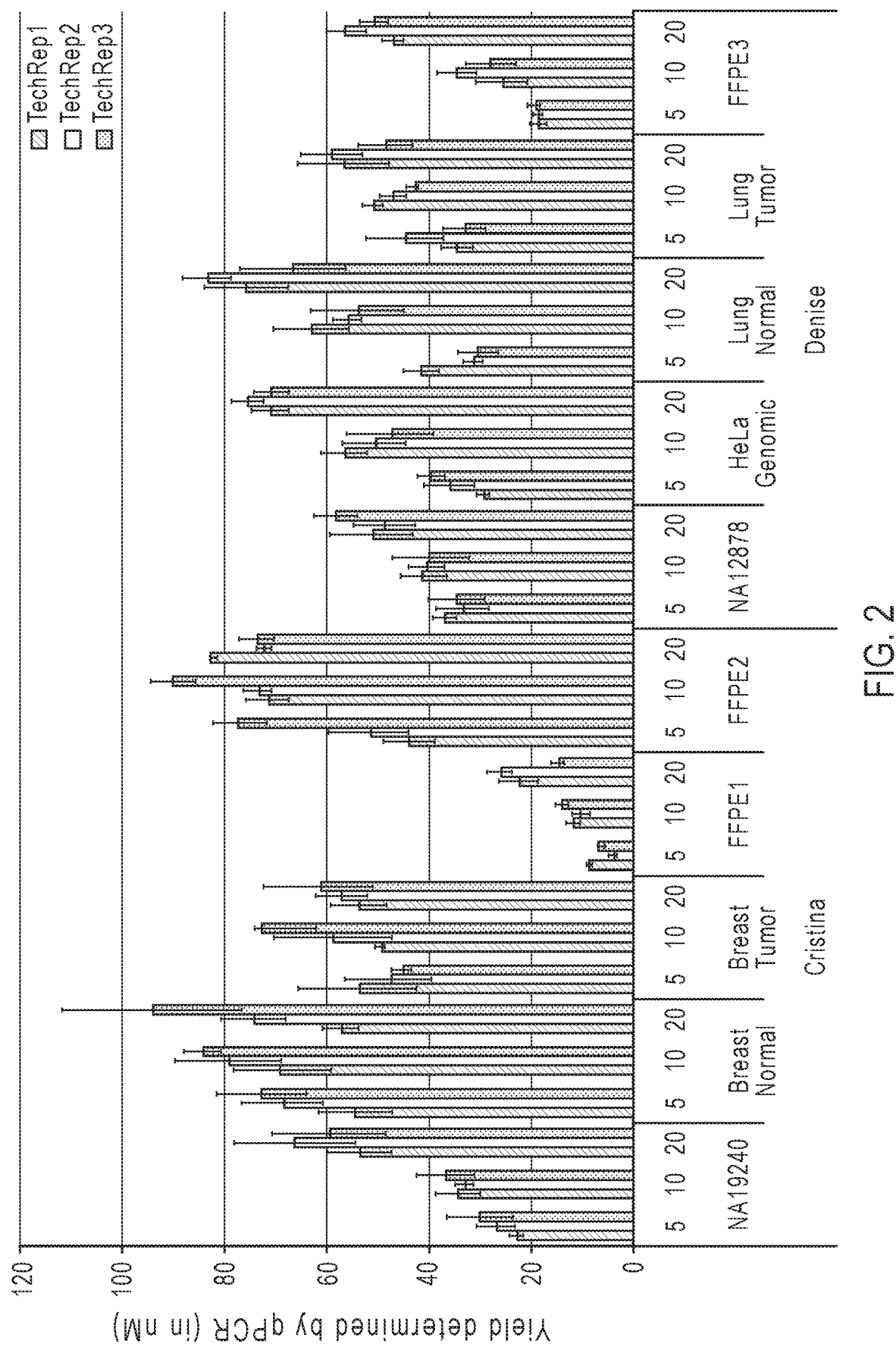
FIG. 2 is a schematic depicting exemplary results obtained using a non-limiting embodiment of the target nucleic acid molecule enrichment method.
Figure 3:
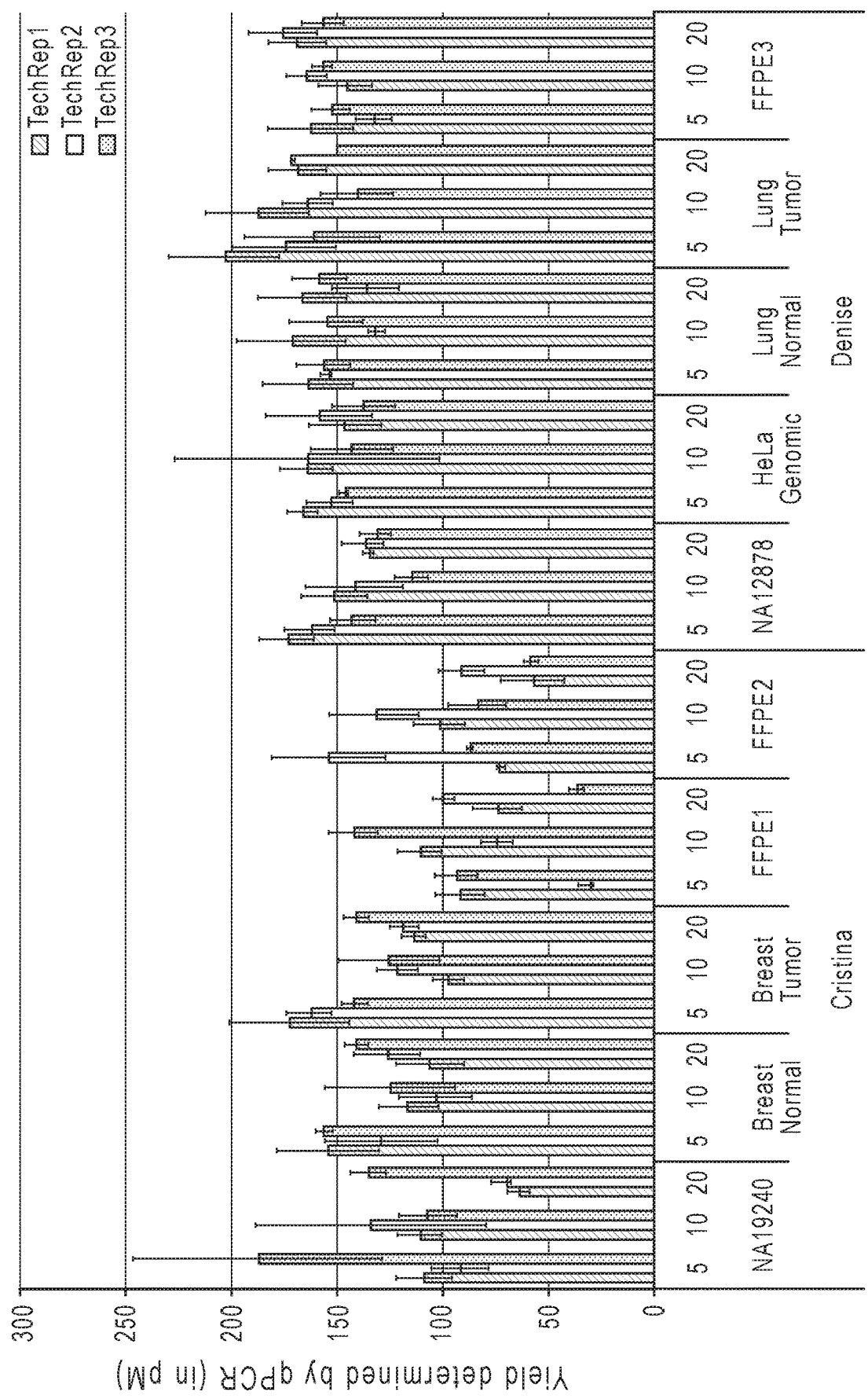
FIG. 3 is schematic depicting exemplary results obtained using a non-limiting embodiment of the target nucleic acid molecule enrichment method.

FIGS. 2 and 3 are representative data obtained from 10 DNA samples (2 matched lung normal/tumor pairs, 3 formalin-fixed paraffin embedded DNA samples (FFPE), and 3 high molecular weight DNAs) that were carried through a 207-plex amplicon library preparation workflow using 5 ng, 10 ng, and 20 ng of DNA input. Libraries were prepared in triplicate for each sample at each input level.

Sequencing of these nucleic acid libraries showed no adverse effects on accuracy (>99.5%), uniformity of amplicon representation (>99%), or bases with no strand bias (>99%).

Methods and Materials

Ten human DNA samples (2 matched lung normal/tumor pairs, 3 FFPE samples, and 3 high molecular weight reference DNAs) were carried through the Ion AmpliSeq 2.0 Library Preparation workflow (Ion Ampliseg™ Library Preparation, Publication Part Number MAN0006735, Life Technologies, CA) using the Ion Ampliseg™ Cancer Hotspot Panel v2 (Life Technologies, CA, Cat. No. 4475346) starting with 5, 10, and 20 ng for each DNA sample. The Ion Ampliseg™ Cancer Hotspot Panel is a 207-plex cancer panel primer pool used to perform multiplex PCR for preparation of amplicon libraries from genomic "hotspot" regions that are frequently mutated in human cancer genes.

Briefly, the workflow was as follows. All temperature incubations were in a PCR thermocycler (except for room temperature). Reagents were from the Ion AmpliSeq™ Library Kit 2.0 (Life Technologies, CA, Cat. No. 4480441), unless otherwise noted.

Amplicons were produced by "pre-amplification" in 20 μL reactions consisting of 1× Ion AmpliSeq™ HiFi Master Mix (sold as a component of the Ion Ampliseg™ Library Kit 2.0, Cat. No. 4480441), 1× Ion Ampliseg™ Cancer Hotspot Panel v2 primers (Life Technologies, CA, Cat. No. 4475346), and either 5 ng, 10 ng, or 20 ng human genomic DNA. Each DNA sample was pre-amplified in triplicate at each input level. Reactions were distributed to individual wells of a 96 well PCR plate (MicroAmp® Optical 96-Well Reaction Plate, Life Technologies, CA, Cat. No. N8010560), the plate sealed and incubated as follows: 2 minutes at 99° C., then 20 cycles (for FFPE samples) or 17 cycles of 15 seconds at 99° C. and 4 minutes at 60° C., after which the thermocycler was held at 10° C.

Amplicons from pre-amplification were prepared for ligation by treatment with Ion FuPa Reagent (2 μL blend/well) (sold as a component of the Ion Ampliseg™ Library Kit 2.0, Cat. No. 4480441) for 10 minutes at 50° C., 10 minutes at 55° C., 10 minutes at 60° C., then held at 10° C.

Ligation of sequencing adapters was achieved by addition of 4 μL Switch Solution (sold as a component of the Ion Ampliseg™ Library Kit 2.0, Cat. No. 4480441), 2 μL Ion Ampliseg™ Adapters (sold as a component of the Ion Ampliseg™ Library Kit 2.0, Cat. No. 4480441), and 2 μL DNA ligase (sold as a component of the Ion Ampliseg™ Library Kit 2.0, Cat. No. 4480441) to each well, followed by incubation for 30 minutes at 22° C., 10 minutes at 72°, then held at 10° C.

Ligated amplicons were purified by addition of 45 μL (1.5× volume) AMPure XP Kit (Beckman Coulter, Cat. No. A63880) to each well, incubation for 5 min at room temperature, then drawing the AMPure beads into pellets by placing the PCR plate on a plate magnet (DynaMag™-96 Side, Life Technologies, Cat. No. 12331D) for 2 minutes.

Supernatants were removed by pipet and 150 μL of 70% ethanol (v/v in water) was added to each well. Pellets were washed by toggling the plate position two times in the magnet to move pellets from side to side in the wells. Wash was removed by pipet and the washing was repeated a second time for each well. Following removal of the second wash, the pellets were allowed to dry for 5 minutes at room temperature, then re-suspended in 50 μL Library Amplification Primer Mix (a mixture of Platinum PCR SuperMix High Fidelity (sold as a component of the Ion Ampliseg™ Library Kit 2.0, Cat. No. 4480441) plus Equalizer primers (provided at a concentration of 400 pM).

The plate was returned to the magnet for 2 minutes, the supernatants were removed to clean the wells, the plate was sealed and incubated for 2 minutes at 98° C., followed by eight cycles of 15 seconds at 98° C. and 1 minute at 60° C., and then held at 10° C. An aliquot (2 μL) of each amplified nucleic acid library was diluted for in-process quantitation by qPCR using the Ion Library Quantitation Kit (Life Technologies, CA, Cat. No. 4468802) according to the instructions.

Amplified libraries were normalized directly out of the library amplification process described above, without purification, by addition of 25 μL Equalizer Capture oligonucleotide (final concentration 133 pM), incubation for 5 minutes at room temperature, addition of 5 μL DynaBeads MyOne streptavidin C1 beads (sold as a component of the Ion Ampliseg™ Library Kit 2.0, Cat. No. 4480441)(washed and re-suspended in two volumes Equalizer Wash Buffer (10 mM Tris pH 8, 500 mM NaCl, 0.1M EDTA, 0.05% Tween-20), incubation for 5 minutes at room temperature, followed by pelleting the DynaBeads on a plate magnet as described above. Supernatants were removed by pipet and 150 μL/well Equalizer Wash Buffer was added to each well. Pellets were washed by toggling the plate position three times in the magnet to move pellets from side to side in the wells. Wash was removed by pipet and the washing was repeated a second time for each well. Following removal of the second wash, the pellets were re-suspended in 50 μL Equalizer Elution Buffer (10 mM Tris pH 8, 0.1 mM EDTA and 0.1 μg/μL glycogen) and the plate was returned to the magnet for 2 minutes. The supernatants containing normalized libraries were removed to clean wells. Aliquots of each library were diluted for quantitation by qPCR using the Ion Library Quantitation Kit (Life Technologies, CA, Cat. No. 4468802) according to the manufacturer's instructions.

Results:

Quantitation of Libraries by qPCR Prior to Normalization.

Aliquots of all libraries were diluted 5,000-fold and assayed in triplicate by qPCR with the Ion Library Quantitation Kit (Life Technologies, CA, Cat. No. 4468802) according to the manufacturer's instructions. Total library yields ranged from 4-94 nM after library amplification and prior to normalization (FIG. 2).

Quantitation of Libraries by qPCR after Normalization.

Aliquots of all libraries were diluted 100-fold and assayed in triplicate by qPCR with the Ion Library Quantitation Kit (Life Technologies, CA, Cat. No. 4468802) according to the manufacturer's instructions. Final library yields after normalization ranged from 33-204 pM, with 84/90 (93%) libraries within 70-200 pM (FIG. 3).

What is claimed:

1. A method for isolating a specific amount of nucleic acid from a sample, comprising:
    a) generating a population of bound target nucleic acid molecules by contacting a sample including a population of target nucleic acid molecules with a plurality of hairpin primers which include a first and a second primer sequence separated by a non-replicable moiety, wherein the second primer sequence binds a portion of the target nucleic acid molecules, wherein the first primer sequence binds capture oligonucleotides, and wherein the capture oligonucleotides includes a capture moiety;
    b) contacting the first primer sequence to a limiting number of capture oligonucleotides under conditions where at least some of the capture oligonucleotides hybridize to at least some of the first primer sequences; and c) forming a population of captured target nucleic acid molecules by capturing a substantial portion of the population of bound target nucleic acid molecules, wherein the number of captured target nucleic acid molecules is directly proportional to the limiting number of capture oligonucleotides.

2. The method of claim 1, further comprising contacting the population of bound target nucleic acid molecules with a binding agent.

3. The method of claim 2, wherein the binding agent includes a support.

4. The method of claim 3, wherein the support comprises a bead.

5. The method of claim 2, wherein the binding agent comprises streptavidin.

6. The method of claim 2, further comprising subjecting the captured nucleic acid molecules to non-permissive conditions to elute the captured nucleic acid molecules from the binding agent, thereby forming a population of eluted target nucleic acid molecules.

7. The method of claim 1, wherein the capture moiety comprises biotin.

8. The method of claim 1 wherein the first and second primer sequences of the hairpin primer are substantially complementary to each other and have a first Tm.

9. The method of claim 8 further comprising extending the hairpin primer in a template-dependent fashion to form a primer extension product having a single stranded region including the first primer sequence before forming the population of captured target nucleic acid molecules.

10. The method of claim 9 wherein the capture oligonucleotide includes a sequence that is substantially complementary to at least a portion of the single stranded region of the primer extension product.

11. The method of claim 9 wherein the extending is performed at a temperature that is significantly above the first Tm, such that the first and second primer sequences of the hairpin primer do not substantially hybridize to each other.

12. The method of claim 9 wherein the primer extension product is hybridized to the capture oligonucleotide at a temperature significantly below the first Tm, such that substantially all unextended hairpin oligonucleotide is in the hairpin form.

13. The method of claim 9 wherein hybridizing the primer extension product to a capture oligonucleotide that includes a capture moiety and selectively capturing the primer extension product uses a binding agent that selectively binds to the capture moiety.

14. A method for isolating a specific amount of nucleic acid of two or more nucleic acid samples, comprising: forming a first population of captured target nucleic acid molecules from a first sample according to the method of claim 1, and forming a second population of captured target nucleic acid molecules from a second sample according to the method of claim 1, wherein the number of captured target nucleic acid molecules in the first and second populations of captured target nucleic acid molecules vary by no greater than 5-fold from each other.

* * * * *